(12) United States Patent
Schafer et al.

(10) Patent No.: US 8,876,869 B1
(45) Date of Patent: Nov. 4, 2014

(54) POLYAXIAL BONE SCREW ASSEMBLY

(75) Inventors: Andrew Schafer, Ramona, CA (US);
Robert German, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/311,490

(22) Filed: Dec. 5, 2011

Related U.S. Application Data (63) Continuation of application No. 13/019,944, filed on Feb. 2, 2011, now abandoned, which is a continuation of application No. 12/820,136, filed on Jun. 21, 2010, now abandoned.

(60) Provisional application No. 61/218,864, filed on Jun. 19, 2009.

(51) Int. Cl.
*A61B 17/70* (2006.01)

(52) U.S. Cl.
CPC ......... *A61B 17/7032* (2013.01); *A61B 17/7082* (2013.01)
USPC .......................................... 606/278; 606/86 A (58) Field of Classification Search
CPC .................... A61B 17/7032; A61B 2019/30
USPC .................................................. 606/246–279
See application file for complete search history.

(56) References Cited

U.S. PATENT DOCUMENTS

| | | |
|---|---|---|
| 5,002,542 A | 3/1991 | Frigg |
| 5,047,029 A | 9/1991 | Aebi |
| 5,196,013 A | 3/1993 | Harms et al. |
| 5,209,752 A | 5/1993 | Ashman et al. |
| 5,380,323 A * | 1/1995 | Howland ...................... 606/278 |
| 5,443,467 A | 8/1995 | Biedermann et al. |
| 5,476,464 A | 12/1995 | Metz-Stavenhagen et al. |
| 5,501,684 A | 3/1996 | Hess et al. |
| 5,549,608 A | 8/1996 | Errico et al. |
| 5,575,791 A | 11/1996 | Lin |
| 5,584,831 A | 12/1996 | McKay |
| 5,609,593 A | 3/1997 | Errico |
| 5,681,319 A | 10/1997 | Biedermann |
| 5,697,929 A * | 12/1997 | Mellinger ...................... 606/270 |
| 5,728,097 A | 3/1998 | Mathews |
| 5,728,098 A | 3/1998 | Drewry et al. |
| 5,735,851 A * | 4/1998 | Errico et al. .................. 606/266 |
| 5,741,255 A | 4/1998 | Krag |
| 5,752,957 A | 5/1998 | Ralph et al. |
| 5,810,818 A | 9/1998 | Errico |
| 5,879,350 A | 3/1999 | Sherman et al. |
| 5,938,663 A | 8/1999 | Petreto |

(Continued)

FOREIGN PATENT DOCUMENTS

AU 723894 B2 2/1999
CA 2045502 5/1991

(Continued)

*Primary Examiner* — Eduardo C Robert
*Assistant Examiner* — Stuart S Bray
(74) *Attorney, Agent, or Firm* — Jonathan Spangler; Rory Schermerhorn (57) ABSTRACT

The present invention involves a system and methods for assembling and implanting a polyaxial bone screw assembly. The polyaxial bone screw assembly includes, but is not necessarily limited to, a bone screw that can be initially secured to a bony structure and subsequently have a receiver assembly attached to the implanted bone screw. Additionally, a closure structure is a part of the polyaxial bone screw assembly and functions to secure an elongate member within the receiver assembly.

15 Claims, 9 Drawing Sheets

(56) References Cited

U.S. PATENT DOCUMENTS

| | | | |
|---|---|---|---|
| 5,976,135 A | 11/1999 | Sherman et al. | |
| 6,004,349 A * | 12/1999 | Jackson | 606/270 |
| 6,063,090 A * | 5/2000 | Schlapfer | 606/270 |
| 6,074,391 A | 6/2000 | Metz-Stavenhagen et al. | |
| 6,083,226 A | 7/2000 | Fiz | |
| 6,106,526 A | 8/2000 | Harms et al. | |
| 6,123,706 A | 9/2000 | Lange | |
| 6,132,432 A | 10/2000 | Richelsoph | |
| 6,179,838 B1 | 1/2001 | Fiz | |
| 6,183,473 B1 | 2/2001 | Ashman | |
| 6,187,005 B1 | 2/2001 | Brace | |
| 6,210,413 B1 | 4/2001 | Justis | |
| 6,224,596 B1 * | 5/2001 | Jackson | 606/264 |
| 6,231,575 B1 | 5/2001 | Krag | |
| 6,248,105 B1 | 6/2001 | Martin et al. | |
| 6,251,112 B1 * | 6/2001 | Jackson | 606/916 |
| 6,258,090 B1 * | 7/2001 | Jackson | 606/916 |
| 6,280,442 B1 | 8/2001 | Barker et al. | |
| 6,402,749 B1 | 6/2002 | Ashman | |
| 6,454,773 B1 | 9/2002 | Sherman et al. | |
| 6,471,703 B1 | 10/2002 | Ashman | |
| 6,485,494 B1 | 11/2002 | Haider | |
| 6,520,962 B1 | 2/2003 | Taylor et al. | |
| 6,554,834 B1 * | 4/2003 | Crozet et al. | 606/65 |
| 6,623,485 B2 | 9/2003 | Doubler et al. | |
| 6,626,906 B1 | 9/2003 | Young | |
| 6,648,887 B2 | 11/2003 | Ashman | |
| 6,660,004 B2 * | 12/2003 | Barker et al. | 606/328 |
| 6,685,705 B1 | 2/2004 | Taylor | |
| 6,716,214 B1 * | 4/2004 | Jackson | 606/266 |
| 6,802,844 B2 | 10/2004 | Ferree | |
| 6,835,196 B2 | 12/2004 | Biedermann et al. | |
| 6,872,209 B2 | 3/2005 | Morrison | |
| 6,964,666 B2 | 11/2005 | Jackson | |
| 7,022,122 B2 | 4/2006 | Amrein et al. | |
| 7,066,939 B2 | 6/2006 | Taylor | |
| 7,083,622 B2 | 8/2006 | Simonson | |
| 7,179,261 B2 * | 2/2007 | Sicvol et al. | 606/86 A |
| 7,211,087 B2 | 5/2007 | Young | |
| 7,476,239 B2 * | 1/2009 | Jackson | 606/266 |
| 7,731,736 B2 * | 6/2010 | Guenther et al. | 606/273 |
| 7,857,834 B2 * | 12/2010 | Boschert | 606/269 |
| 7,914,558 B2 * | 3/2011 | Landry et al. | 606/246 |
| 7,985,242 B2 * | 7/2011 | Forton et al. | 606/246 |
| 8,012,181 B2 * | 9/2011 | Winslow et al. | 606/257 |
| 8,021,398 B2 * | 9/2011 | Sweeney et al. | 606/269 |
| 8,034,084 B2 * | 10/2011 | Landry et al. | 606/265 |
| 8,043,341 B2 * | 10/2011 | Zhao et al. | 606/264 |
| 8,100,946 B2 * | 1/2012 | Strausbaugh et al. | 606/266 |
| 8,162,990 B2 * | 4/2012 | Potash et al. | 606/264 |
| 8,167,915 B2 * | 5/2012 | Ferree et al. | 606/279 |
| 8,172,847 B2 * | 5/2012 | Dziedzic et al. | 606/86 A |
| 8,221,472 B2 * | 7/2012 | Peterson et al. | 606/270 |
| 8,241,341 B2 * | 8/2012 | Walker et al. | 606/306 |
| 8,277,490 B2 * | 10/2012 | Freeman et al. | 606/266 |
| 2004/0138662 A1 * | 7/2004 | Landry et al. | 606/61 |
| 2004/0143265 A1 * | 7/2004 | Landry et al. | 606/61 |
| 2004/0147928 A1 * | 7/2004 | Landry et al. | 606/61 |
| 2004/0172022 A1 * | 9/2004 | Landry et al. | 606/61 |
| 2004/0260284 A1 * | 12/2004 | Parker | 606/61 |
| 2005/0085813 A1 * | 4/2005 | Spitler et al. | 606/61 |
| 2005/0277927 A1 * | 12/2005 | Guenther et al. | 606/61 |
| 2005/0277928 A1 | 12/2005 | Boschert | |
| 2006/0025771 A1 | 2/2006 | Jackson | |
| 2006/0036244 A1 * | 2/2006 | Spitler et al. | 606/61 |
| 2006/0084993 A1 * | 4/2006 | Landry et al. | 606/61 |
| 2006/0095035 A1 * | 5/2006 | Jones et al. | 606/57 |
| 2006/0095038 A1 | 5/2006 | Jackson | |
| 2006/0100622 A1 | 5/2006 | Jackson | |
| 2006/0111712 A1 | 5/2006 | Jackson | |
| 2006/0111715 A1 | 5/2006 | Jackson | |
| 2006/0142761 A1 * | 6/2006 | Landry et al. | 606/61 |
| 2006/0149232 A1 | 7/2006 | Sasing | |
| 2006/0149233 A1 * | 7/2006 | Richelsoph | 606/61 |
| 2006/0149240 A1 | 7/2006 | Jackson | |
| 2006/0155277 A1 * | 7/2006 | Metz-Stavenhagen | 606/61 |
| 2006/0179244 A1 | 8/2006 | Goodman et al. | |
| 2006/0200133 A1 | 9/2006 | Jackson | |
| 2006/0200136 A1 | 9/2006 | Jackson | |
| 2006/0241603 A1 | 10/2006 | Jackson | |
| 2006/0247631 A1 | 11/2006 | Ahn et al. | |
| 2006/0271047 A1 | 11/2006 | Jackson | |
| 2006/0276789 A1 | 12/2006 | Jackson | |
| 2006/0276792 A1 | 12/2006 | Ensign et al. | |
| 2007/0016200 A1 | 1/2007 | Jackson | |
| 2007/0043378 A1 * | 2/2007 | Kumar et al. | 606/104 |
| 2007/0049933 A1 | 3/2007 | Ahn et al. | |
| 2007/0055240 A1 | 3/2007 | Matthis et al. | |
| 2007/0055241 A1 | 3/2007 | Matthis et al. | |
| 2007/0055244 A1 | 3/2007 | Jackson | |
| 2007/0088357 A1 | 4/2007 | Johnson et al. | |
| 2007/0093818 A1 | 4/2007 | Biedermann et al. | |
| 2007/0118123 A1 * | 5/2007 | Strausbaugh et al. | 606/61 |
| 2007/0123862 A1 | 5/2007 | Warnick | |
| 2007/0123870 A1 | 5/2007 | Jeon et al. | |
| 2007/0167949 A1 | 7/2007 | Altarac et al. | |
| 2007/0173819 A1 | 7/2007 | Sandlin | |
| 2007/0270810 A1 | 11/2007 | Sanders | |
| 2008/0045955 A1 * | 2/2008 | Berrevoets et al. | 606/61 |
| 2008/0051780 A1 | 2/2008 | Vaidya et al. | |
| 2008/0091213 A1 * | 4/2008 | Jackson | 606/99 |
| 2008/0183214 A1 * | 7/2008 | Copp et al. | 606/265 |
| 2008/0221583 A1 * | 9/2008 | Sharifi-Mehr et al. | 606/104 |
| 2008/0306525 A1 * | 12/2008 | Mitchell et al. | 606/246 |
| 2008/0306540 A1 * | 12/2008 | Mitchell et al. | 606/254 |
| 2008/0306541 A1 * | 12/2008 | Mitchell et al. | 606/254 |
| 2008/0306542 A1 * | 12/2008 | Mitchell et al. | 606/254 |
| 2009/0005814 A1 * | 1/2009 | Miller et al. | 606/246 |
| 2009/0138044 A1 * | 5/2009 | Bergeron et al. | 606/246 |
| 2009/0163963 A1 * | 6/2009 | Berrevoets | 606/86 A |
| 2009/0204155 A1 * | 8/2009 | Aschmann | 606/264 |
| 2010/0234891 A1 * | 9/2010 | Freeman et al. | 606/266 |
| 2011/0046683 A1 * | 2/2011 | Biedermann et al. | 606/305 |
| 2011/0137350 A1 * | 6/2011 | Stad et al. | 606/264 |
| 2011/0313476 A1 * | 12/2011 | McLean | 606/86 A |
| 2011/0319943 A1 * | 12/2011 | Donahoe et al. | 606/290 |
| 2012/0035663 A1 * | 2/2012 | Jackson | 606/266 |
| 2012/0123477 A1 * | 5/2012 | Landry et al. | 606/264 |
| 2012/0226317 A1 * | 9/2012 | Potash | 606/264 |
| 2012/0239090 A1 * | 9/2012 | Abdou | 606/264 |
| 2013/0289623 A1 * | 10/2013 | Potash | 606/278 |

FOREIGN PATENT DOCUMENTS

| | | |
|---|---|---|
| WO | 98/32386 | 7/1998 |
| WO | 98/52482 | 11/1998 |
| WO | 2006/029373 | 3/2006 |
| WO | 2008/013892 | 1/2008 |

* cited by examiner

POLYAXIAL BONE SCREW ASSEMBLY

CROSS-REFERENCE TO RELATED APPLICATIONS

This application is a continuation of U.S. patent application Ser. No. 13/019,944, filed Feb. 2, 2011, now abandoned which is a continuation of U.S. patent application Ser. No. 12/820,136, filed Jun. 21, 2010, now abandoned which claims the benefit of priority from U.S. Provisional Patent Application Ser. No. 61/218,864, filed on Jun. 19, 2009, the entire contents of which are each hereby expressly incorporated by reference into this disclosure as if set forth in its entirety herein.

FIELD

The present invention relates generally to medical devices and methods generally aimed at spinal surgery. In particular, the disclosed system and associated methods relate to performing spinal fixation with the use of polyaxial bone screws.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the sacral and coccygeal regions of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. If a disruption to the spine becomes severe enough, damage to a nerve or part of the spinal cord may occur and can result in partial to total loss of bodily functions (e.g. walking, talking, and breathing, etc. . . . ). Therefore, it is of great interest and concern to be able to both correct and prevent any ailments of the spine.

Fixation systems are often surgically implanted into a patient to aid in the stabilization of a damaged spine or to aid in the correction of other spinal geometric deformities. Spinal fixation systems are often constructed as framework stabilizing a particular section of the spine. Existing systems often use a combination of rods, plates, pedicle screws and bone hooks for fixing the framework to the affected vertebrae. The configuration required for each patient varies due to the patient's specific anatomical characteristics and ailments. For example, pedicle screws are often made available in a number of different size shanks (including lengths and widths), can be cannulated or non-cannulated, and may be designed to capture different size rods. Thus, the number of pedicle screws that may need to be provided in order to account for all desired combinations can be very costly and space prohibited.

Spinal fixation systems are often used as an adjunct to spinal fusion procedures in which implants are positioned within an intervertebral disc space to restore a desired height and/or alignment between the upper and lower vertebrae. Ultimately, bone growth across the disc space fuses the vertebrae together thereby maintaining the restored height and/or alignment. Spinal fixation systems are often used to maintain the vertebrae in the corrected position until the bone has had time to fully fuse. In many cases, the fusion implants are positioned first and the spinal fixation systems are placed subsequently. In some instances, this is necessitated by the surgical approach (e.g. anterior, posterior, lateral, etc. . . . ) and in some cases this is necessitated by the fixation system. For example, in posterior lateral interbody fusion (PLIF) and transforaminal interbody fusion (TLIF) procedures, the general size of the polyaxial pedicle screws in common use today can inhibit access to disc space if they are implanted prior to disc space preparation and implant positioning. This need to prepare the disc space and implant the interbody implant prior positioning the fixation system limits the options available to the surgeon.

The fixation system described herein is directed at eliminating, or at least improving upon, the shortcomings of the prior art.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The polyaxial bone screw assembly disclosed herein boasts a variety of inventive features and components that warrant patent protection, both individually and in combination.

Figure 1:
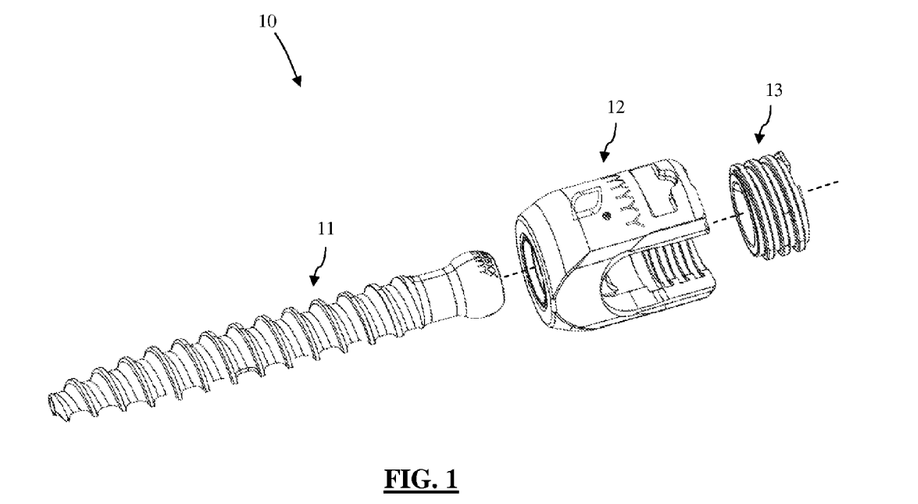
FIG. 1 is a perspective view of one example of a polyaxial bone screw assembly, according to one embodiment of the present invention.

FIG. 1 illustrates an example of a polyaxial bone screw assembly 10 according to one embodiment of the present invention. The polyaxial bone screw assembly 10 includes a bone screw 11, a receiver assembly 12, and a closure structure 13. The bone screw 11 of the present invention is configured to attach securely within a bony structure (e.g. pedicle of a vertebra) and to allow a receiver assembly 12 to attach to the bone screw 11 after placement of the bone screw 11 within the bony structure. It is also possible for the receiver assembly 12 to be attached to the bone screw 11 prior to placement of the bone screw 11 within the bony structure. The receiver assembly 12 and bone screw 11 are configured to engage in such a way that they that the receiver assembly 12 may initially rotate through a range of articulations or rotational alignments (i.e. polyaxial motion) relative to the bone screw 11, and subsequently, be secured in any single position within the range of articulation. The receiver assembly 12 is configured to receive an elongate structure (e.g. a rod) and the closure structure 13 is designed to secure the elongate structure within the receiver assembly 12. The polyaxial engagement between the receiver assembly 12 and bone screw 11 facilitates positioning of the elongate structure within the housing. Once the elongate member is captured within the receiver assembly 12, the closure structure 13 is engaged to lock the elongate structure in the receiver assembly 12 and fix the angular orientation of the receiver assembly 12 and the bone screw 11.

Figure 2:
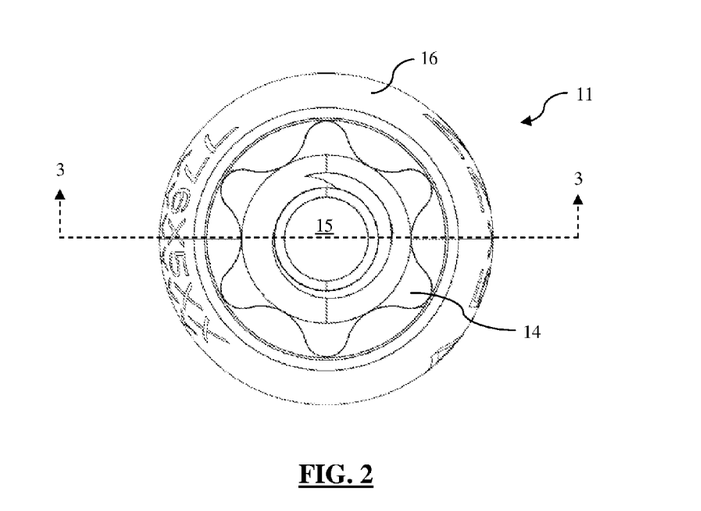
FIG. 2 is a top view of a bone screw forming a part of the polyaxial bone screw assembly of FIG. 1.
Figure 3:
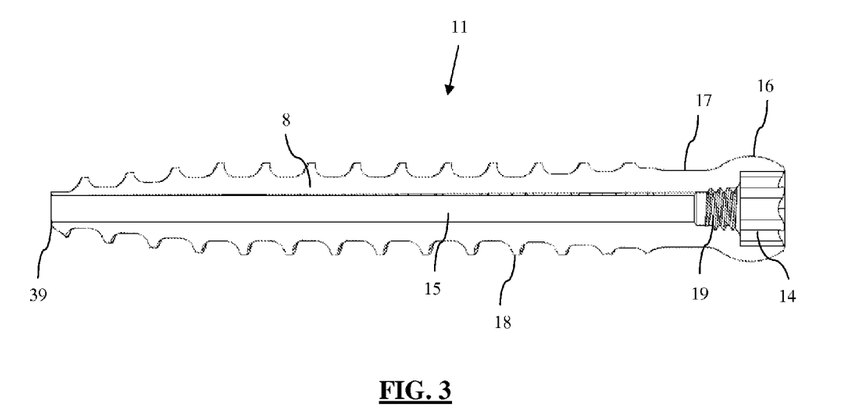
FIG. 3 is a cross section view of the bone screw of FIG. 2 taken along line 3-3 of FIG. 2.

FIGS. 2 and 3 illustrate an example embodiment of a bone screw 11. The bone screw 11 of the polyaxial bone screw assembly 10 is comprised of a neck 17, a shank 8, and a capture structure 16. At least one bone implantable thread 18 extends radially from the shank 8 and functions to secure the placement of the bone screw 11 within a bony structure. Preferably, the bone screw 11 may be provided as part of a kit including screws of various length and diameter combinations. By way of example, the bone screw 11 may have a length approximately in the range of 0.78 in to 2.56 in and an outer diameter approximately in the range 0.18 in to 0.33 in. The capture structure 16 includes at least one internal thread 19 and a tool engaging feature 14. Both the internal thread 19 and tool engaging feature 14 can be used, for example, to engage and attach various tooling for aligning and advancing the bone screw 11 into a bony structure. The bone screw 11 may have a cannulated core 15 that travels longitudinally generally along the centerline of the shank 8 and extends throughout the entire length of the bone screw 11. This allows, for example, the bone screw 11 to be passed over of k-wire or other guide to aid in placement during surgery. Though not shown, the bone screw 11 may also be provided in non-cannulated embodiments. The generally spherical shape of the capture structure 16 permits it (by way of example) to articulate freely within the generally spherical pocket within the receiver assembly 12, which will be discussed in greater detail below. The surface of the capture structure 16 may be textured (e.g. scored or knurled) for enhancing frictional engagement with the retaining and articulating structure 40.

Figure 4:
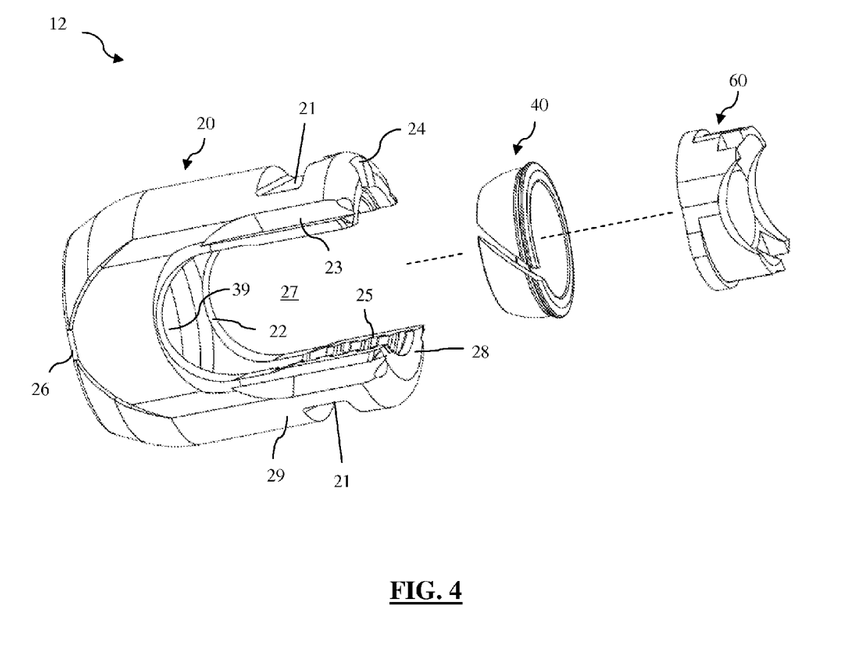
FIG. 4 is an exploded view of the receiver assembly forming a part of the polyaxial bone screw assembly of FIG. 1.

FIG. 4 illustrates an example embodiment of a receiver assembly 12. The receiver assembly 12 is typically provided in an assembled state (best shown in FIG. 9) and includes a receiver 20, a retaining and articulating structure or collar 40, and a cradle 60. The receiver 20 has a generally U-shaped appearance with a generally cylindrical inner profile and a faceted outer profile. A base 26, with a pair of upstanding arms 29 forms a U-shaped cradle which define U-shaped openings 27 through the faceted sides of the receiver 20. Receivers may be provided in a variety of dimensions depending on the size and shape of the elongate member that it will be in secured frictional engagement with. For example, the receivers 20 are preferably provided with dimensions suitable for capturing elongate structures ranging between approximately 0.21 and 0.26 in. According to one preferred example, receivers 20 are provided in a kit having receivers dimensioned to receive elongate elements approximately 0.21 in and receivers dimensioned to receive elongate elements approximately 0.24 in in diameter. By way of example, the outer diameter of the receiver 20 is generally about 0.5 in in diameter regardless of the associated rod dimension. Both arms 29 have at least one helical wound guide and advancement structure 25 at least partially situated along their internal walls beginning from the top surface 28 end of the receiver 20. The guide and advancement structure 25 of the receiver 20 are configured to mate with at least one exterior helically wound guide and advancement structure 72 of the closure structure 13, locking the elongate structure within the receiver 20.

Figure 9:
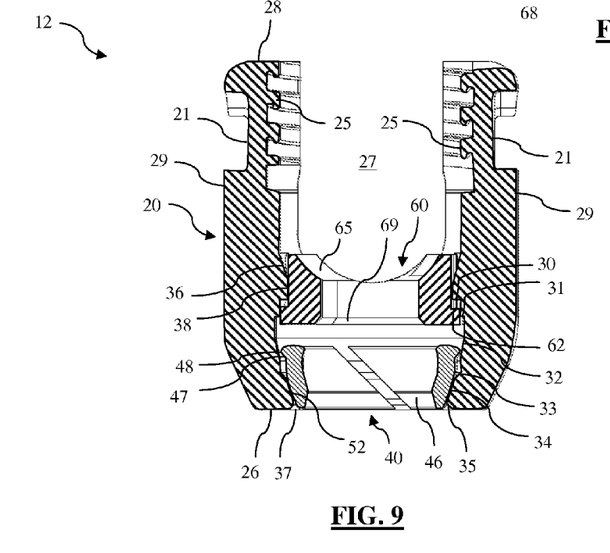
FIG. 9 is a cross section view of the receiver assembly forming a part of the polyaxial bone screw assembly of FIG. 1.
Figures 10, 11:
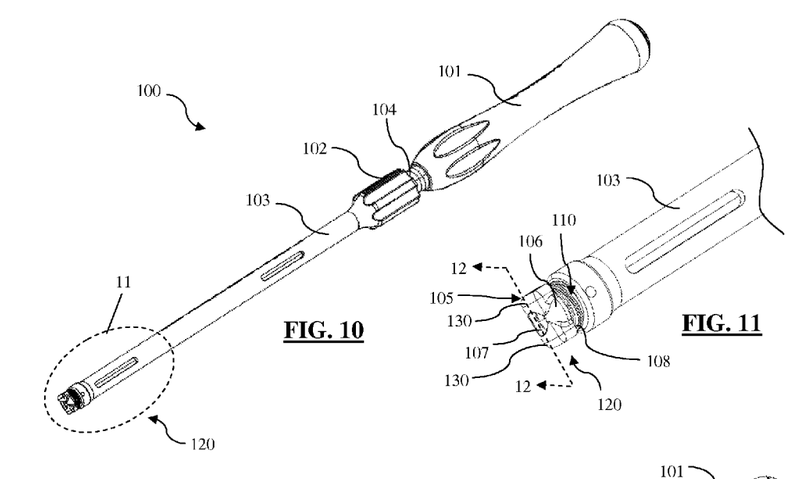
FIG. 10 is a perspective view of one example of an inserter, according to one embodiment of the present invention.
FIG. 11 is a partial view of the inserter taken from partial view area 11 of FIG. 10.
Figures 12, 13:
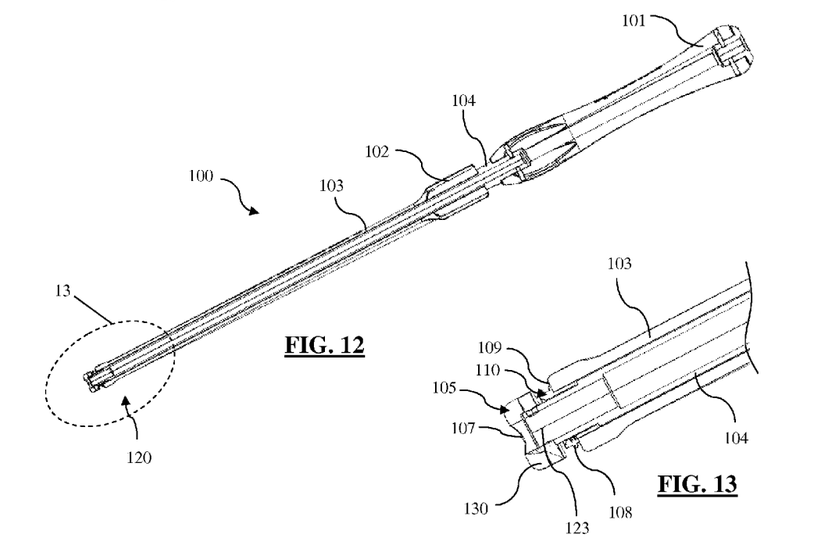
FIG. 12 is a cross section view of the inserter of FIG. 10 taken along line 12-12 of FIG. 11.
FIG. 13 is a partial view of the inserter taken from partial view area 13 of FIG. 12.
Figure 14:
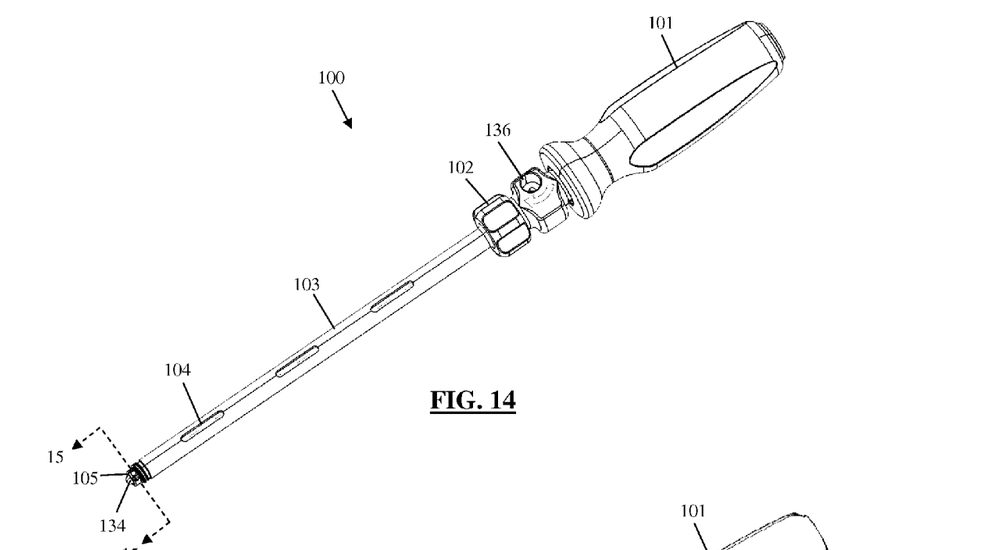
FIG. 14 is a perspective view of another example embodiment of an inserter integrating a verification device for assessing the adequacy of the coupling between the receiver and bone screw.

The outer surface of the receiver 20 includes tooling attachment features, such as, for example, grip bores 21 on the outer surface of both arms 29 and radially located recessed slots 23 on the sides of both arms 29 adjacent the u-shaped openings 27. These tooling attachment features permit the attachment of a variety of tools used for positioning and attachment of the receiver assembly 12 to the bone screw 11. With reference to FIG. 9, additional features of the receiver 20 include two steps 38 extending inwardly from the inside walls of the arms 29 (with one step 38 situated on each arm 29). By way of example only, each step 38 spans at least a portion of the inside wall of an arm 29 and are positioned generally 180 degrees apart from each other. Located within the base 26 of the receiver 20 is a cavity defined by a generally spherical surface, radial concave support 34, which is sized and shaped for slidable mating and eventual frictional engagement with the retaining and articulating structure 40, as described below.

Figure 15:
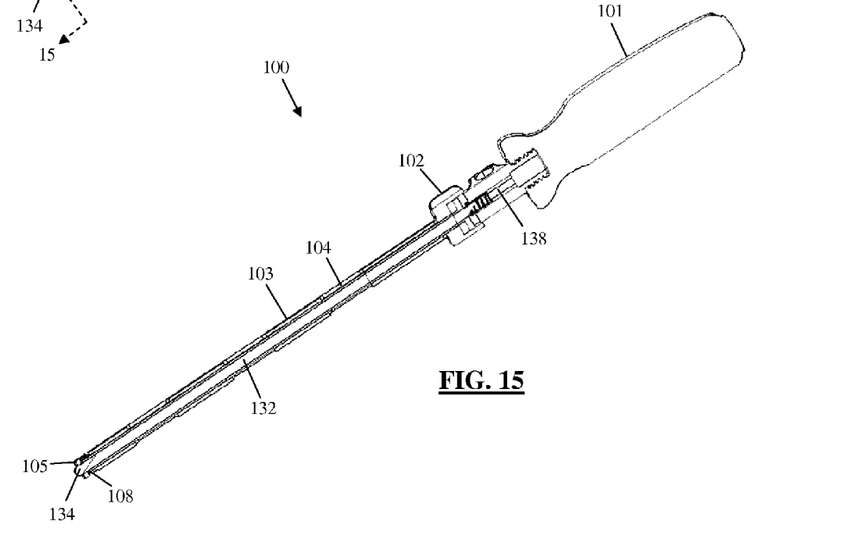
FIG. 15 is a cross section view of the inserter of FIG. 14.
Figure 16:
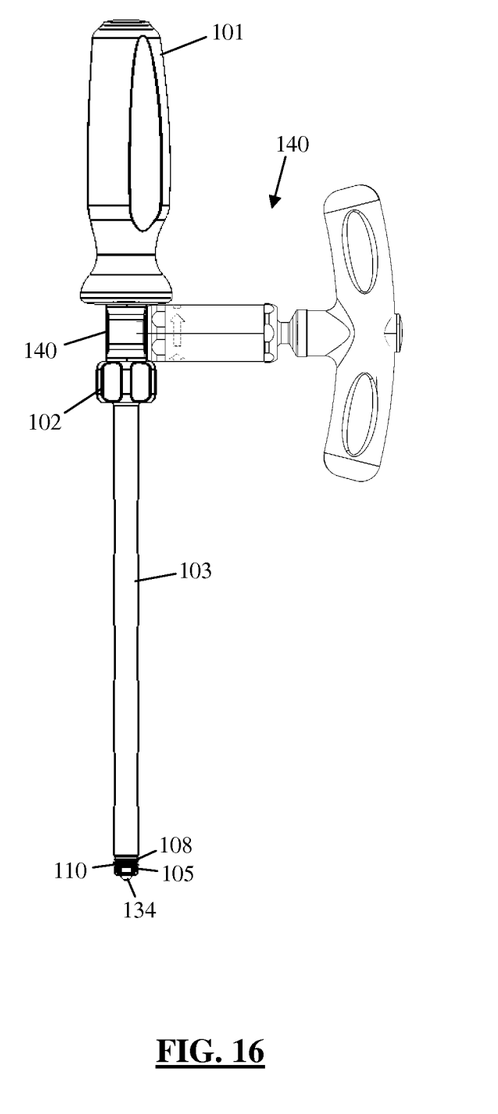
FIG. 16 is a side view of the inserter of FIG. 14 including a separately engageable torque wrench, according to one embodiment of the present invention

According to one example (FIGS. 1, 15, & 16), the closure structure 13 of the polyaxial bone screw assembly 10 is shown by way of example to include a top surface 70, a base 71, and at least one exterior guide and advancement structure 72. The top surface 70 includes at least one generally recessed tool engaging feature 73 which functions to engage a variety of tooling that assist in aligning and securing the closure structure 13 to the receiver assembly 12. A recessed slot 75 on the top surface 70 provides the operator with an aligning mechanism for screwing the closure structure 13 into the receiver 20. For example, aligning the recessed slot 75 of the closure structure 13 with the recessed slot 24 of the receiver 20 ensures the interior and exterior guide and advancement structures 25, 72, respectively engage properly when advanced. Positioned centrally within the base 71 of the closure structure 13 is a concave feature 74 for enhanced surface contact between the closure structure 13 and a generally spherical head 82 of a rod 80. The concave feature 74 may have surface features, or surface roughening, to enhance the frictional engagement with the rod head 82. The closure structure 13 also has a base 71 encircling concave feature 74 which can provide a frictional surface for securing the body 81 of a rod 80 within the receiver assembly 12. Surface features, or surface roughening, may also be included on the base 71 of the closure structure 13 to enhance the frictional engagement with the body of the rod.

Figure 5:
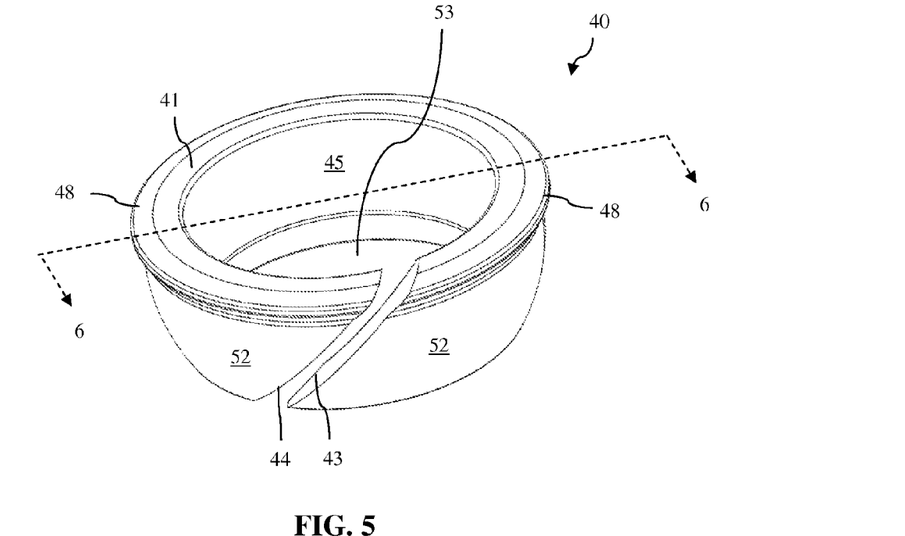
FIG. 5 is a perspective view of the retaining and articulating structure, or collar, forming part of the receiver assembly of FIG. 4.
Figure 6:
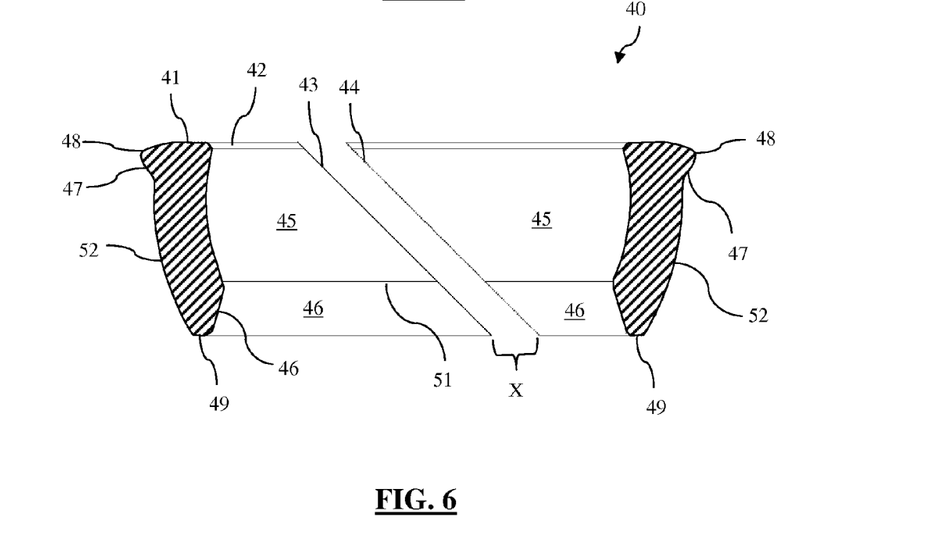
FIG. 6 is a cross section view of the retaining and articulating structure, or collar, of FIG. 5 taken along line 6-6 of FIG. 5.
Figure 7:
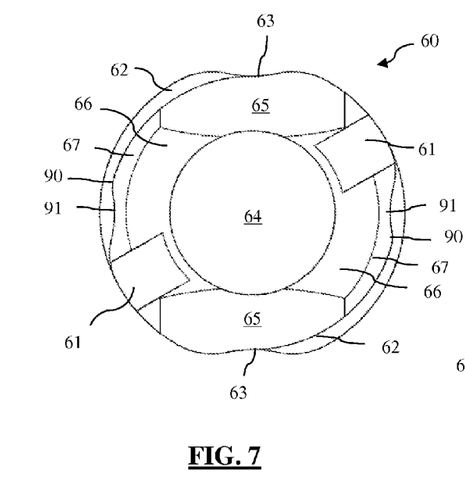
FIG. 7 is a top view of the cradle forming part of the receiver assembly of FIG. 4.
Figure 8:
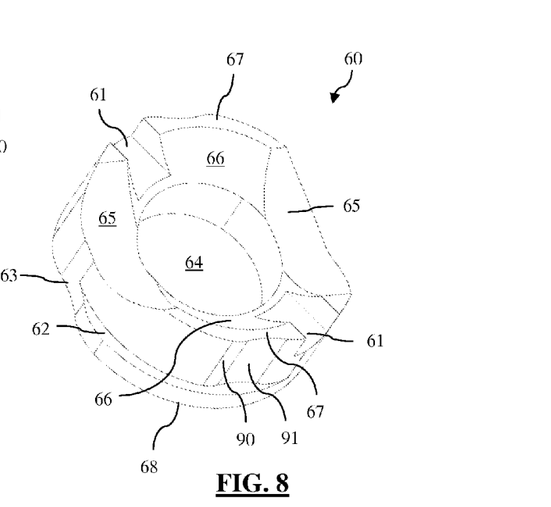
FIG. 8 is a perspective view of the cradle forming part of the receiver assembly of FIG. 4.

FIGS. 5-6 illustrate an example embodiment of a retaining and articulating structure or collar 40. The collar 40 is comprised of a top surface 41, a bottom surface 49, an outer convex surface 52, an inner concave surface 45, and a radial protrusion 48. Notably, the collar 40 is not continuous, and instead includes a slot 44 extending from the top surface 41 to bottom 49. The slot 44 has a width X and allows the collar 40 to be temporarily expanded and compressed to receive the capture structure 16 and to secure the collar 40 around the capture structure 16, as described below. FIGS. 7-8 illustrate an example embodiment of a cradle 60. The cradle 60 is comprised of a top surface 67, spherical inner walls 66, concave supports 65, and a base 68. Additional features of the cradle 60 include first outer diameter notches 63, second outer diameter notches 91, locking protuberances 90, a central opening 64, locking ledges 62, and tool engaging features 61.

To assemble the receiver assembly 12, the collar 40 is inserted through the arms 29 of the receiver 20 until it rests on the steps 38 within the receiver 20. The collar is then forced past the steps 38 by sliding its outer convex surface 52 and radial protrusion 48 along the taper 36 above the steps 38 which causes the collar 40 to circumferentially compress up to the distance X. When the collar 40 is circumferentially compressed, the collar 40 is able to travel past the steps 38 in the direction of the bottom surface 26 of the receiver 20. Once the collar 40 has completely traveled past the steps 38, the collar 40 is able to returns back to its natural shape (so that the space between the first and second break surfaces 43, 44 returns to a distance of approximately X) and is then confined from exiting the receiver 20. Therefore, the first ledge 30 acts as a stop against the top surface 41 of the collar 40 and does not allow the collar 40 to travel towards the top surface 41 of the receiver 20. In the other direction (towards the bottom surface 26 of the receiver 20), the radial taper 33 and radial concave support 34 both prevent the complete passage of the collar 40 through the central opening 37 of the receiver 20. Even when the collar 40 is in its circumferentially compressed state, the collar 40 cannot exit the receiver 20 through its central opening 37. Once the collar is in place, the cradle is positioned such that the bottom surface 62 of the cradle 60 is facing the top surface 28 of the receiver 20. The cradle 60 is then placed into the center of the receiver 20 (between the arms 29) until the cradle 60 rests generally circumferentially within the round inner walls of the receiver 20 and the base 68 of the cradle 60 sits on the taper 36 of the steps 38. The cradle 60 is then aligned (a tool may be engaged into the tool engaging features 61 to accomplish this) so that the first outer diameter notches 63 of the cradle 60 are aligned over the steps 38 of the receiver 20. This allows the cradle 60 to travel past the steps 38 towards the bottom surface 26 of the receiver 20 until the base 68 of the locking ledges 62 rest against the inside wall of the receiver 20 and prevent the cradle 60 from traveling further down towards the bottom surface 26 end of the receiver 20. At this point, the cradle 60 can be rotated along its central axis (e.g. in the clockwise direction) so that the locking ledges 62 travel beneath the steps 38 of the receiver 20. The cradle 60 is rotated again until the steps 38 are forced past the locking protuberances 90 of the cradle 60 and the steps 38 are situated within the second outer diameter notches 91. When the steps 38 of the receiver are situated within the second outer diameter notches 91, the cradle 60 is permanently secured into place and the receiver assembly 12 is generally complete (and best shown in FIG. 9).

FIGS. 10-13 illustrate an example of an embodiment of an inserter 100. The inserter 100 is comprised of a proximal handle 101, a distal handle 102, a first shaft 104, a second shaft 103, and an engagement end 120. The proximal handle 101 is rigidly connected to the proximal end 121 of the first shaft 104 and provides a rigid grasping element for the user. At the distal end 123 of the first shaft 104 is the engagement head 105 which is rigidly attached to the first shaft 104. The first shaft 104 is shown, by way of example, to be cannulated, and a center hole 107 at the distal end of the engagement head 105 travels through the engagement head 105. The continuous through hole formed between the cannulated first shaft 104 and the center through hole 107 of the engagement head 105 allows extended elements (e.g. tooling, wires) to travel generally the length of the inserter 100 through its center. Alternatively, inserter 100 may be uncannulated. The distal handle 102 is rigidly connected to the proximal end 122 of the second shaft 104 and both are free to slidably rotate about their central axis over the outer diameter of the first shaft 104. A guide and advancement feature 110 situated at the distal end 109 of the second shaft 104, which has at least one helical guide and advancement structure 108 extending radially outward beginning at its distal end.

The inserter 100 is utilized, for example, to securely engage the receiver assembly 12 and attach the receiver assembly 12 to a bone screw 11. The shape of the engagement head 105 allows it to slide into the open end of the receiver 20 with the engagement head 105 wings 106 generally conforming to the rounded inside walls of the arms 29. The ends 130 of the engagement head 105 are shaped to fit within the U-shaped openings 27 of the receiver 20 and enforce anti-rotation of the engagement head 105 in relation to the receiver 20. Once the engagement head 105 has been placed within the U-shaped openings 27, the guide and advancement feature 110 can then be engaged to at least one guide and advancement structure 25 of the receiver 20. To engage at least one helical guide and advancement structure 108, the user would, for example, grasp the proximal handle 101 with one hand and rotate the distal handle 102 in a direction that causes at least one helical guide and advancement structure 108 to engage with at least one guide and advancement structure 25 of the receiver 20. The interlocked configuration between at least one guide and advancement structure 25 of the receiver 20 and at least one helical guide and advancement structure 108 of the guide and advancement feature 110 enforce longitudinal fixation between the inserter 100 and the receiver 20. Once the receiver assembly 12 is longitudinally and rotationally fixed (shown in FIG. 17A), the user is then able to securely attach the receiver assembly 12 to the capture structure 16 of the bone screw 11, as described below. According to an additional embodiment of inserter 100, an additional verification shaft 132 is integrated into the inserter. The verification shaft 132 allows the user to test the attachment of the receiver assembly 12 to the bone screw 11 and ensure that the receiver assembly 12 is fully seated on the capture structure 16. The verification shaft 132 passes through the center of the first shaft 104 such that a distal end 134 can extend beyond engagement head 105 of the first shaft when the verification shaft is extended. A torque wrench is engaged with a drive piece 136 situated at the proximal end 138 of the verification shaft 132. When the engagement head 105 of the first shaft 104 is seated in the U-shaped openings 27 and the at least one helical guide and advancement structure 108 is engaged with the at least one guide and advancement structure 25 of the receiver, the torque wrench may be operated to drive the verification shaft distally beyond the engagement head 105 and into the cradle 60, creating a pulling force on the receiver assembly 12 relative to the bone screw 11. If the receiver assembly 12 is properly attached to the capture structure 16, the torque wrench will reach its upper limit prior to the receiver assembly 12 popping off the capture structure 16. According to one example, the receiver assembly 12 may be determined to be properly attached if it does not disengage the capture structure 16 when force is applied in the range between 30 and 40 in/lbs. Although not shown, it is also contemplated that an additional tool may be provided to remove the receiver assembly 12 from the capture structure 16 after it has been properly seated. This may allow for in situ correction or adjustment without requiring removal of the entire bone screw assembly.

Figure 17A:
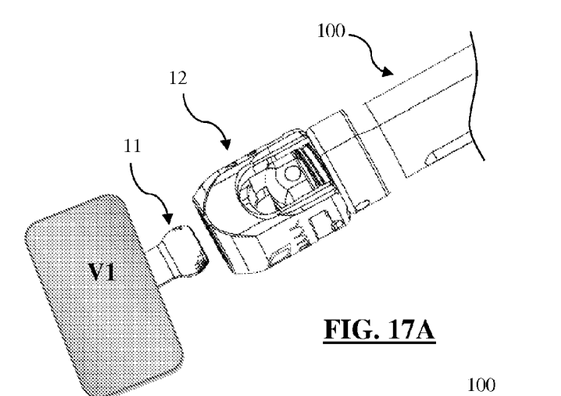
FIG. 17A-17C is a series of side views of the receiver assembly of FIG. 4 engaged with the inserter of FIG. 10 and the process of attaching the receiver assembly to a bone screw that is implanted into a bony structure.
Figure 17B:
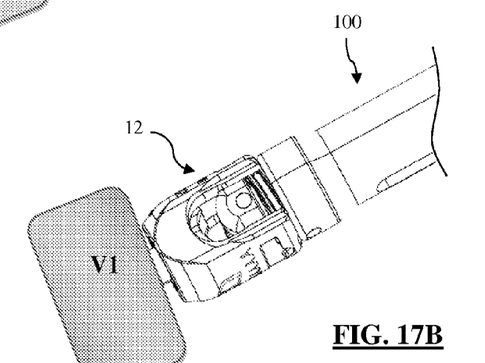
Figure 17C:
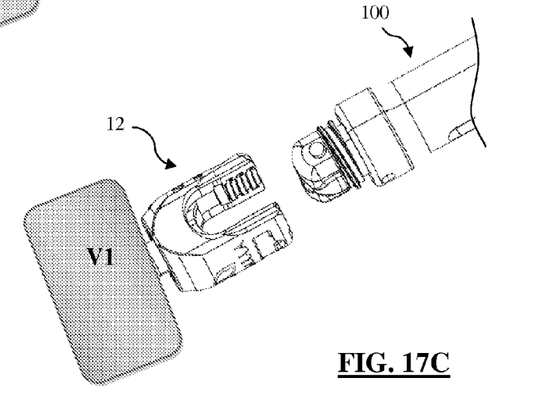

FIGS. 17A-17C illustrate the attachment of the receiver assembly 12 to the bone screw 11. As described above, the receiver assembly 12 is fixed to the engagement end 120 of an inserter 100. FIG. 17A shows a bone screw 11 which has been securely implanted into a bony structure (V1). The capture structure 16 of the bone screw 11 remains exposed, which will ultimately be captured by the receiver assembly 12. Preferably, the capture structure 16 should remain a sufficiently above the bony surface to allow for full articulation of the receiver 20 on the capture member 16 once it is attached. This may be accomplished for example by including a stop on the screw driver (not shown) used for insertion. For example, the screw driver may envelope the capture member and extend along the neck 17 such that the screw 11 cannot be inserted too deep. Alternatively, or in addition, a reamer or similar bone preparation tool may be provided to remove bone around the capture structure 16. With the bone screw implanted in the boney structure, the user aligns the central opening 37 of the receiver 20 generally concentrically with the spherical capture structure 16 of the bone screw 11. The operator can then direct the receiver assembly 12 in the direction of the capture structure 16 and cause the capture structure 16 to pass through the central opening 37 of the receiver 20. The chamfered internal edge 35 of the central opening 37, which also has a larger diameter than the capture structure 16, allows the capture structure 16 to gently pass through the central opening 37 of the receiver 20.

As the capture structure 16 passes through the central opening 37 it pushes the collar 40 upwards into the base 26 until the collar 40 is pushing up against the base 68 of the cradle 60. With the collar 40 resting above the internal edge 35 of the central opening 37, the capture structure 16 can advance past the inner chamfer 46 of the collar 40, forcing the collar 40 to increase circumferentially (by further spreading apart the first and second break surfaces 43, 44) until the largest diameter of the capture structure 16 passes through the inner protruding ring 51. Once the capture structure 16 passes through the inner protruding ring 51, the collar 40 returns to its original circumference, or nearly so, and snugly captures the capture structure 16 (best shown in FIG. 19).

Once the receiver assembly 12 has securely captured the capture structure 16 of the bone screw 11 (depicted in FIG. 17B), the inserter 100 can be removed from the receiver assembly 12 by rotating the distal handle 102 relative to the proximal handle 101 to disengage the guide and advancement structure 25. Once the guide and advancement structures 25, 108 are disengaged, the engagement head 105 may be withdrawn from within the receiver 20 (depicted in FIG. 17C).

At this point, the connection between the bone screw 11 and receiver assembly 20 resembles joint with the capture structure 16 being able to slidably rotate within the collar 40 and the generally spherical outer surface of the collar 40 being able to slidably rotate within the confines of the generally spherical features within the cavity of the receiver 20. In this configuration, the collar spherical surfaces slidingly mate with both the capture structure 16 spherical surface and the receiver 20 spherical surface to provide multiple or compound polyaxial articulation, as described in more detail in U.S. Pat. No. 7,476,239, filed May 10, 2005, the entire contents of which are incorporated herein by reference as if set forth herein in its entirety. According to one example, the articulations between the receiver assembly 20 and the bone screw 11 provide about 30 degrees in all directions. Therefore, as a surgeon configures a spinal fixation system using at least one polyaxial bone screw assembly 10, at least one additional bone screw assembly (fixed or polyaxial), and at least one elongate member, the surgeon is able to easily align the elongate member(s) with the receiver assembly 12 of the polyaxial bone screw assembly 10. Moreover, the surgeon may select from and mate together, variously dimensioned bone screws with variously dimensioned receivers in order to form the most optimal spinal support structure configuration. Moreover, the ability to place the bone screw 11 into the boney structure prior to engaging the receiver 20, means that the area around the none screw will not be obstructed by the head. This can provide the advantage, for example, of being able to utilize bone screws 11 secured in the disc space to distract he disc space for preparation and implant insertion without obstructing the working corridor. By way of example, a distraction tool, such as that described in detail in Pending U.S. application Ser. No. 12/378,936, filed Feb. 20, 2009, may be engaged with the implanted bone screws 11 and utilized to force the bone screws 11, and hence the vertebrae in which they are engaged apart. Thereafter, the disc space can be prepared, implant inserted, and then the receivers 20 can be attached and elongate element installed.

Figure 18:
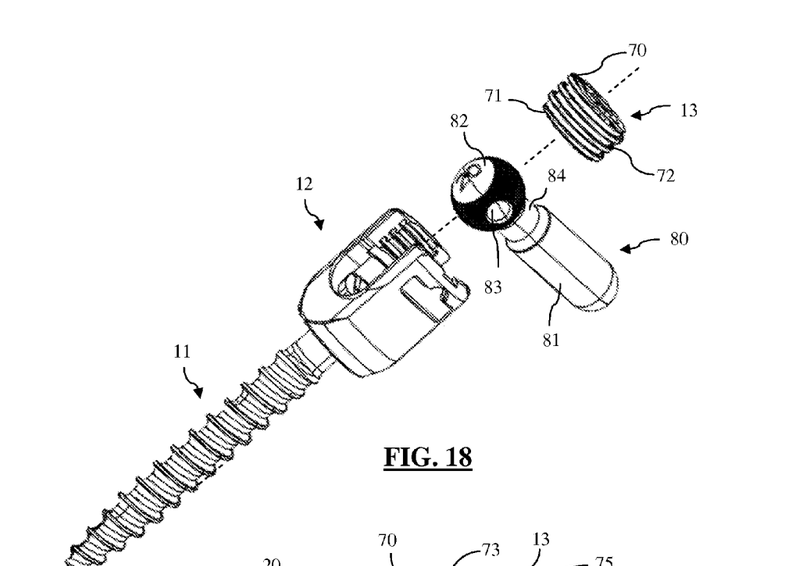
FIG. 18 is an exploded view of the polyaxial bone screw assembly of FIG. 1 capturing a rod.

FIG. 18 illustrates, by way of example, one side of a final construct including, bone screw 11, receiver 20, closure member 13, and an elongate element (rod 80). It should be appreciated that while only one screw is being illustrated, at least a second screw (e.g. the poly axial bone screw 10 or other polyaxial or fixed pedicle screws), and potentially multiple screws will be placed in one or more vertebra surround the first screw. Additionally, screws and constructs may be place contralaterally. In the configuration illustrated in FIG. 18, the spherical head 82 of a rod 80 is inserted into the center of a receiver assembly 12 so that the spherical head 82 rests on the cradle surfaces 65 of the cradle 60 with the neck 84 of the rod 80 extending out from between the U-shaped openings 27. Though not necessary, either or both of the cradle surfaces 65 and/or features of an elongate member (e.g. the head 82 of a rod 80) may have surface features, or surface roughening, to enhance the frictional engagement between the cradle 60 and elongate member for secure positioning. The rod 80 is preferably composed of a metal (e.g. titanium, stainless steel, cobalt chrome etc.), but may also be of a polymer (e.g. polyether-ether-ketone (PEEK)) or any other material suitable for the applications of the present invention.

Notably, the neck 84 of the rod 80 is narrower than the body 81 of the rod 80 and the U-shaped openings 27 so that the body 81 of the rod 80 can be angled in a variety of angles extending out from the receiver 20. A thru hole 83 through the head 82 (and or body 81) of the rod 80 can be used guide advancement of the rod over a k-wire or other guide structure during implantation. While the rod 80 is shown having a single spherical end, it will be appreciated that a rod with two spherical ends may be used. It will also be appreciated that a rod with no spherical ends may be used.

Once the elongate member is placed within the center of the receiver assembly 12, the closure structure 13 can then be attached to the receiver assembly 12 for securing the elongate member in place. As mentioned above, the closure structure 13 is secured to the receiver 20 by interlocking at least one of its guide and advancement structures 72 with at least one interior guide and advancement structure 25 of the receiver 20. As the closure structure 13 is advanced toward the elongate member, it applies force onto the elongate member which in turn applies force onto the cradle 60. As the closure structure 13 continues to advance and capture the elongate structure in the receiver assembly 12, the base 68 of the cradle 60 advances towards the collar 40 and capture structure 16. The base 68 of the cradle 60 will eventually apply force on the capture structure 16 and force the capture structure 16 with the attached collar 40 toward the chamfered internal edge 35 of the receiver 20 which will cause the collar to tighten around the capture structure 16. Ultimately, the frictional engagement between the, capture structure 16, cradle 40, and chamfered edge 35 of receiver locks the receiver 20 in the desired angular position on the bone screw.

Figure 19:
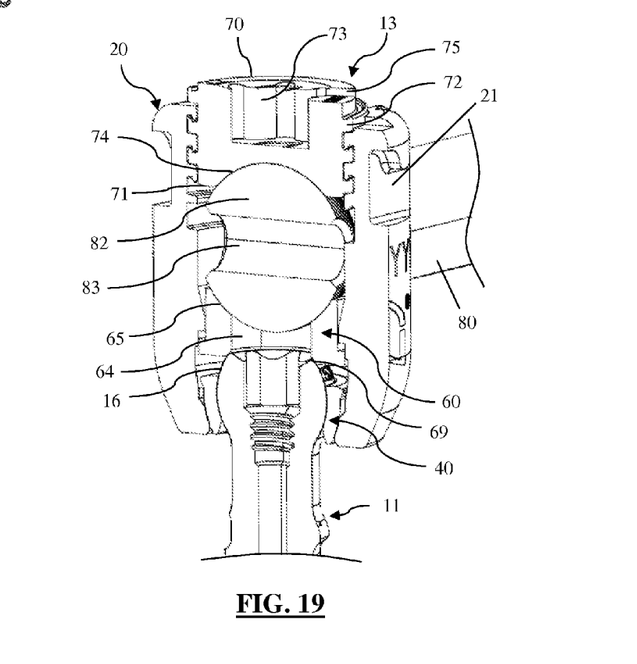
FIG. 19 is a cross section view of the polyaxial bone screw assembly capturing the head of a rod.

FIG. 19 illustrates the assembled state of the construct shown in FIG. 18. The cradle surface 65 of a cradle 60 and the concave surface 74 of the closure structure 13 are shown to be in intimate contact with the outer profile of the head 82 of the rod 80. This intimate contact between the cradle 60 and closure structure 13 with the head 82 of the rod 80 enables the frictional force between these surfaces to secure the positioning of the rod 80 relative to the polyaxial bone screw assembly 10. FIG. 19 also shows the frictional engagement between the base 68 of the cradle 60 and the capture structure 16 of the bone screw 11 and how the inner diameter chamfer 69 of the cradle 60 provides a gentle edge for the top end of the capture structure 16 to interact with. As described above, it is the force applied by the base 68 of the cradle 60 onto the capture structure 16 which forces the capture structure 16 to force the collar 40 (which is securely compressed around the outer diameter of the capture structure 16) into the cavity of the receiver 20 such that the collar 40 is frictionally secured in position, and thus prevents the movement of the bone screw 11 relative to the receiver assembly 12.

Although described with respect to specific examples of the different embodiments, any feature of the polyaxial bone screw disclosed herein by way of example only may be applied to any of the embodiments without departing from the scope of the present invention. Furthermore, procedures described, for example only, involving specific regions of the spine (e.g. thoracic and lumbar) may be applied to another region of the spine without departing from the scope of the present invention and dimensioning of the implant may be adjusted to accommodate any region.

While not specifically described above, it will be understood that various other steps may be performed in using and implanting the devices disclosed herein, including but not limited to creating an incision in a patient's skin, distracting and retracting tissue to establish an operative corridor to the surgical target site, advancing the implant through the operative corridor to the surgical target site, removing instrumentation from the operative corridor upon insertion of the implant, and closing the surgical wound. For example, the bone screw assembly 10 may be particularly useful when performing a minimally invasive TLIF, such as those shown and described (by way of example) in the Pending U.S. application Ser. No. 12/580,214, filed Oct. 15, 2009, U.S. Provisional Application Ser. No. 61/259,825, filed Nov. 10, 2009, the entire contents of which are incorporated by reference as if set forth herein.

While this invention has been described in terms of a best mode for achieving this invention's objectives, it will be appreciated by those skilled in the art that variations may be accomplished in view of these teachings without deviating from the spirit or scope of the invention.

What is claimed is:

1. A system for in situ coupling of a rod receiver portion of a spinal fixation anchor to a bone screw portion of the fixation anchor, comprising:
   a bone screw having a shank engageable within a bone structure in a patient and a partially spherical capture structure;
   a receiver configured for in situ coupling to the bone screw after the bone screw has been anchored to the bone structure, the receiver including a base and a pair of spaced apart arms extending above the base and defining a rod passage dimensioned to receive a spinal fixation rod therein, the base including an interior cavity adjacent a lower opening, the receiver also including a collar situated within the base and configured to receive the capture structure of the bone screw, the collar having an upper edge and a bottom edge, an outer surface, an inner surface, and a slot extending from the upper edge to the bottom edge, the slot permitting expansion of a collar circumference to allow passage of the bone screw capture structure when the collar is advanced over the bone screw capture structure from the bottom edge, the inner surface of the collar having a partially spherical contact surface for articulating engagement with the partially spherical capture structure, wherein the base lower opening has a support surface complementary to the collar outer surface on which the collar rests prior to and after coupling of the receiver and the bone screw, the cavity having a larger circumference above the support surface such that when the collar is advanced over the bone screw capture structure from the bottom edge the collar rises into the cavity where the larger circumference permits expansion of the collar circumference until the partially spherical capture structure rests within the partially spherical contact surface, whereafter the collar descends back into contact with the support surface such that the partially spherical capture structure rests in the collar contact surface and the collar rests in the base support surface in a manner such that the receiver is angularly articulatable relative to the bone screw; and
   a receiver inserter that releasably couples to the receiver for in situ coupling of the receiver and the bone screw, the inserter including a first shaft having a first distal end that engages and holds the receiver relative to the first shaft and a second shaft that operably translates through a passage in the first shaft such that a second distal end of the second shaft extends beyond the first shaft first distal end delivering a translational force to the capture structure relative to the receiver to verify secure coupling between the receiver and the bone screw.

2. The system of claim 1, further comprising a cradle with a lower surface situated in said cavity and an upper surface situated within said rod passage.

3. The system of claim 2, wherein said upper surface of said cradle is configured to mate with a spinal fixation rod and said lower surface is configured to mate with the capture structure.

4. The system of claim 3, wherein the cradle translates within the cavity such that a translation force applied to the cradle is transferred to the capture structure.

5. The system of claim 4, wherein the transfer of force to the capture structure causes friction between the base support structure, collar, and capture structure that inhibits articulation of the receiver relative to the bone screw.

6. The system of claim 5, further comprising a closure element engageable with the spaced apart arms of the receiver configured to capture a spinal fixation rod within the rod passage and press the fixation rod into the cradle.

7. The system of claim 5, wherein guide and advancement features on the closure member engage complementary guide and advancement features on the interior surface of the spaced apart arms.

8. The system of claim 3, wherein said cradle includes locking notches to secure within said receiver.

9. The system of claim 1, wherein said operable translation of said second shaft through the passage of the first shaft is controlled by a torque wrench.

10. The system of claim 9, wherein said torque wrench is set to a predetermined force at which said receiver will not decouple from said bone screw only if said receiver and said bone screw are properly engaged.

11. The system of claim 10, wherein the torque wrench is set to a predetermined force within the range of 30 in/lbs to 40 in/lbs.

12. The system of claim 1, wherein a guide and advancement feature on the first distal end engages a complementary guide and feature on the interior surface of the spaced apart arms to engage and hold the receiver relative to the first shaft.

13. The system of claim 12, wherein the first distal end further includes a pair of wing extensions situated below the guide and advancement feature and dimensioned to sit in the rod passage between the space apart arms to prevent rotation of the receiver relative to the first shaft.

14. The system of claim 1, wherein said collar outer surface and said support surface are partially spherical.

15. The system of claim 1, wherein said collar is angularly articulable relative to said support surface.

* * * * *